United States Patent [19]

Discenzo et al.

[11] Patent Number: 6,023,961
[45] Date of Patent: Feb. 15, 2000

[54] MICRO-VISCOSITY SENSOR AND LUBRICATION ANALYSIS SYSTEM EMPLOYING THE SAME

[75] Inventors: Frederick M. Discenzo, Brecksville; Chung-Chiun Liu, Cleveland Heights; Donald L. Feke, Chesterland; Laurie Ann Dudik, South Euclid, all of Ohio

[73] Assignee: Reliance Electric Industrial Company, Cleveland, Ohio

[21] Appl. No.: 09/054,117

[22] Filed: Apr. 2, 1998

[51] Int. Cl.[7] .............................. G01N 9/00; G01N 11/16
[52] U.S. Cl. ...................... 73/54.01; 73/54.24; 73/54.41; 73/61.79; 422/68.1
[58] Field of Search .......................... 422/68.1; 73/54.01, 73/54.24, 54.41, 64.53, 61.79

[56] References Cited

U.S. PATENT DOCUMENTS

| | | | |
|---|---|---|---|
| 2,837,913 | 6/1958 | Rich et al. | 73/59 |
| 3,256,741 | 6/1966 | Wise | 73/432 |
| 3,393,553 | 7/1968 | Kleinschmidt | 73/54 |
| 4,200,541 | 4/1980 | Kinner et al. | 252/12.2 |
| 4,675,662 | 6/1987 | Kondo et al. | 340/631 |
| 4,782,332 | 11/1988 | Cipris et al. | 340/603 |
| 4,783,987 | 11/1988 | Hager et al. | 73/32 A |
| 4,792,791 | 12/1988 | Cipris et al. | 340/603 |
| 4,798,738 | 1/1989 | Yafuso et al. | 427/2 |
| 4,922,745 | 5/1990 | Rudkin et al. | 73/32 A |
| 4,926,682 | 5/1990 | Holm-Kennedy et al. | 73/54 |
| 4,935,040 | 6/1990 | Goedert | 55/197 |
| 4,941,346 | 7/1990 | Suzuki et al. | 73/54 |
| 5,004,583 | 4/1991 | Guruswamy et al. | 422/58 |
| 5,038,893 | 8/1991 | Willner et al. | 184/7.4 |
| 5,151,110 | 9/1992 | Bein et al. | 55/75 |
| 5,199,298 | 4/1993 | Ng et al. | 73/54.01 |
| 5,200,027 | 4/1993 | Lee et al. | 156/651 |
| 5,359,881 | 11/1994 | Kalotay et al. | 73/54.06 |
| 5,417,821 | 5/1995 | Pyke | 204/153.1 |
| 5,418,058 | 5/1995 | Li et al. | 428/327 |
| 5,485,491 | 1/1996 | Salnick et al. | 376/245 |
| 5,487,313 | 1/1996 | Johnson | 73/863.71 |
| 5,572,328 | 11/1996 | Fouckhardt et al. | 356/440 |
| 5,581,028 | 12/1996 | Barth et al. | 73/204.26 |
| 5,614,830 | 3/1997 | Dickert et al. | 324/553 |
| 5,633,809 | 5/1997 | Wissenbach et al. | 364/510 |
| 5,644,395 | 7/1997 | Folta | 356/246 |
| 5,646,039 | 7/1997 | Northrup et al. | 435/287.2 |
| 5,660,728 | 8/1997 | Saaski et al. | 210/251 |
| 5,662,165 | 9/1997 | Tubel et al. | 166/250.01 |
| 5,852,229 | 12/1998 | Josse et al. | 73/24.06 |

OTHER PUBLICATIONS

Karagounis, et al. "A Pd–PdO Film Potentiometric pH Sensor", IEEE Transactions on Biomedical Engineering, vol. BME–33, No., 2, Feb. 1986.

Berkeley MicroInstruments, Microviscometer Model BMV100, Jan. 1998.

Primary Examiner—Hezron Williams
Assistant Examiner—J. David Wiggins
Attorney, Agent, or Firm—Himanshu S. Amin; John M. Miller; John J. Horn

[57] ABSTRACT

A micro-viscosity sensor for measuring the viscosity of a lubricant. The micro-viscosity sensor including at least one finger-like element or an array of finger-like elements vertically extending from the surface of a semiconductor base, the at least one finger-like element being oscillated at a desired frequency. The power required to oscillate the at least one-finger-like element is monitored because the power required is a function of the viscosity of the lubricant. The sensor also includes a temperature detector, wherein the thermal conductivity of the temperature detector varies in correspondence with the temperature of the lubricant. A first set of electrical contacts provides for electrical connection to the at least one finger-like element; and a second set of electrical contacts provides for electrical connection to the temperature detector. The viscosity of the lubricant is determined based on the temperature of the lubricant correlated with the power required to oscillate the at least one-finger like element at a particular frequency.

36 Claims, 15 Drawing Sheets

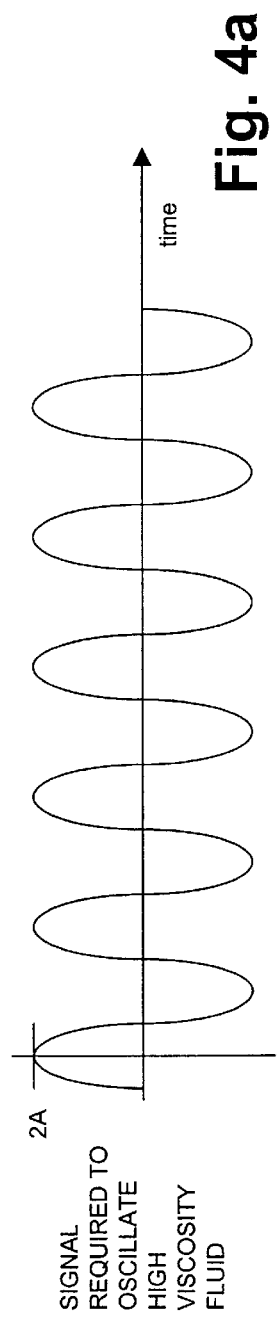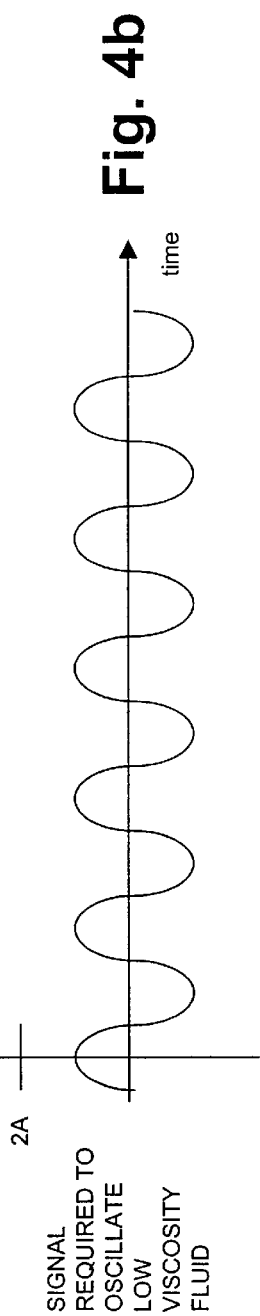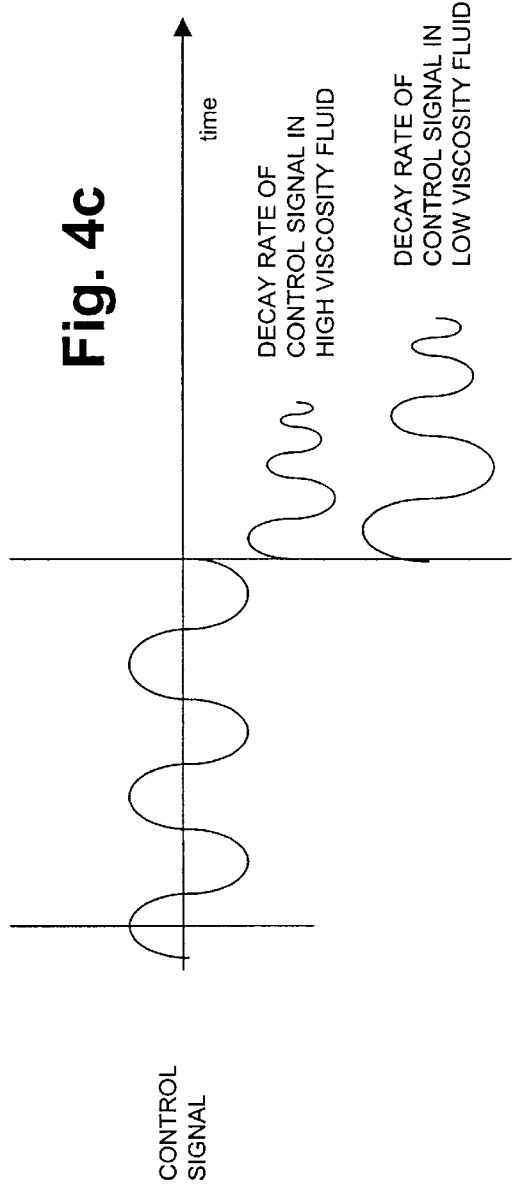

Fig. 5a (200)

| | $f_0$ | $f_1$ | $f_2$ | • | • | • | $f_n$ |
|---|---|---|---|---|---|---|---|
| $TEMP_1$ | $A_3/V_3$ | $A_1/V_1$ | $A_{75}/V_{75}$ | • | • | • | $A_K/V_K$ |
| $TEMP_2$ | $A_{34}/V_{34}$ | $A_{50}/V_{50}$ | $A_{56}/V_{56}$ | • | • | • | $A_F/V_F$ |
| • | $A_{56}/V_{56}$ | $A_{44}/V_{44}$ | $A_{94}/V_{94}$ | • | • | • | $A_H/V_H$ |
| • | $A_{78}/V_{78}$ | $A_{23}/V_{23}$ | $A_{29}/V_{29}$ | • | • | • | $A_B/V_B$ |
| • | $A_{37}/V_{37}$ | $A_{76}/V_{76}$ | $A_{19}/V_{19}$ | • | • | • | $A_D/V_D$ |
| $TEMP_N$ | $A_{67}/V_{67}$ | $A_{88}/V_{88}$ | $A_{47}/V_{47}$ | • | • | • | $A_Y/V_Y$ |

Fig. 5b (210)

| | $P_0$ | $P_1$ | $P_2$ | • | • | • | $P_n$ |
|---|---|---|---|---|---|---|---|
| $TEMP_1$ | BAD V | BAD V | BAD V | BAD V | BAD V | BAD V | BAD V |
| $TEMP_2$ | GOOD V | BAD V | GOOD V | BAD V | BAD V | BAD V | BAD V |
| • | BAD V | BAD V | BAD V | GOOD V | BAD V | BAD V | BAD V |
| • | GOOD V | GOOD V | BAD V | GOOD V | GOOD V | GOOD V | GOOD V |
| • | GOOD V | GOOD V | BAD V | GOOD V | GOOD V | GOOD V | GOOD V |
| $TEMP_N$ | BAD V | GOOD V | GOOD V | GOOD V | GOOD V | GOOD V | GOOD V |

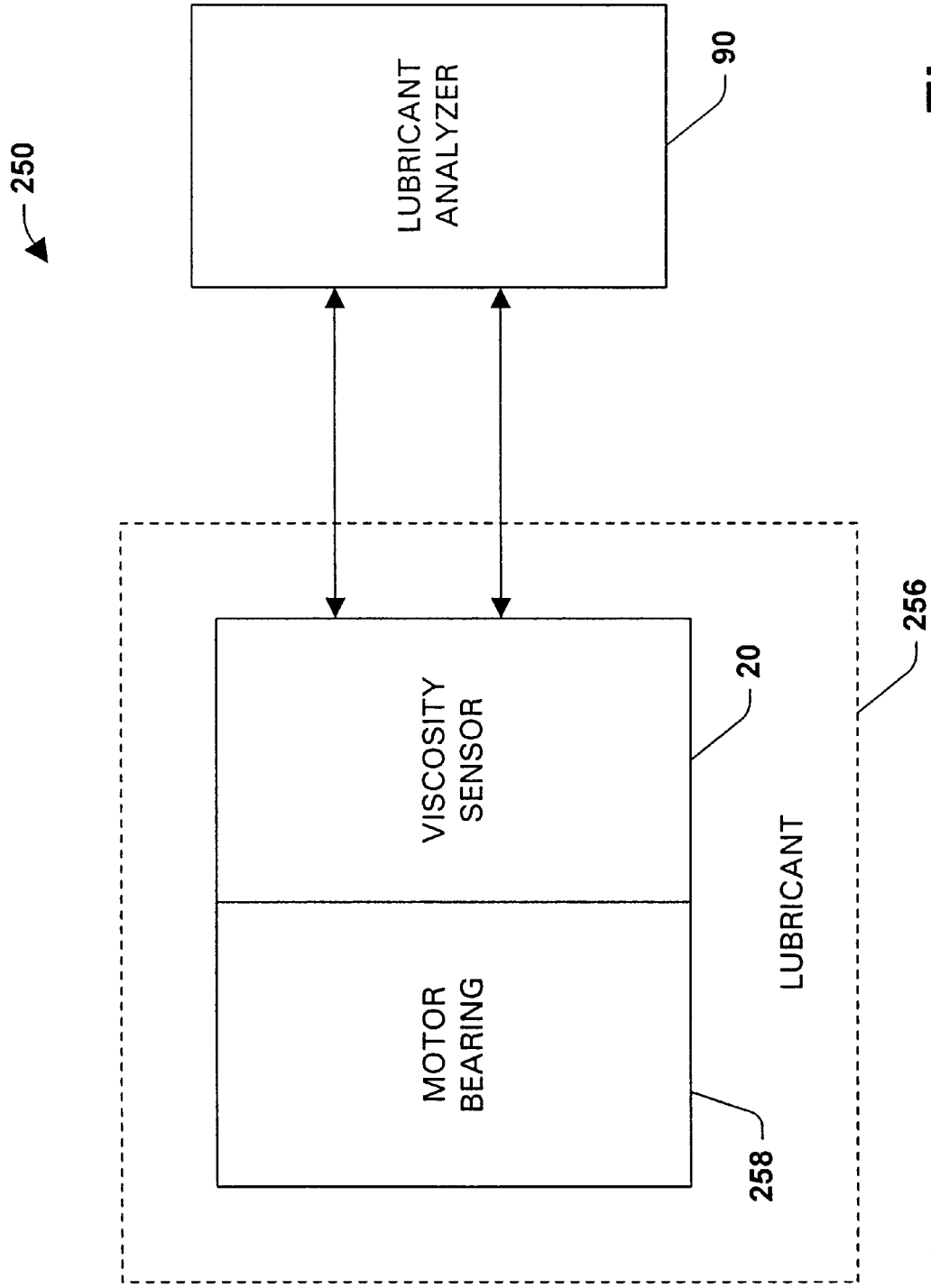

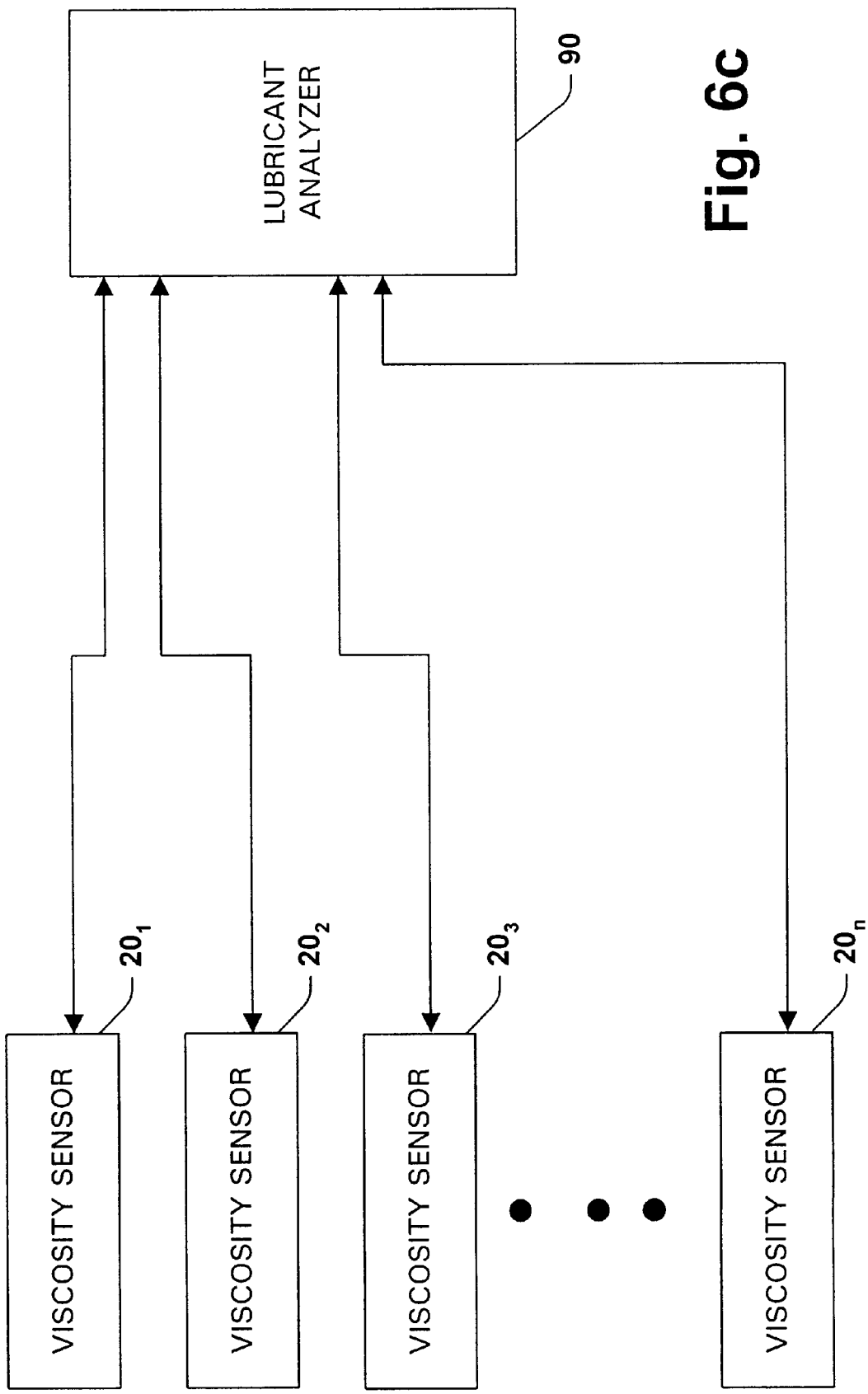

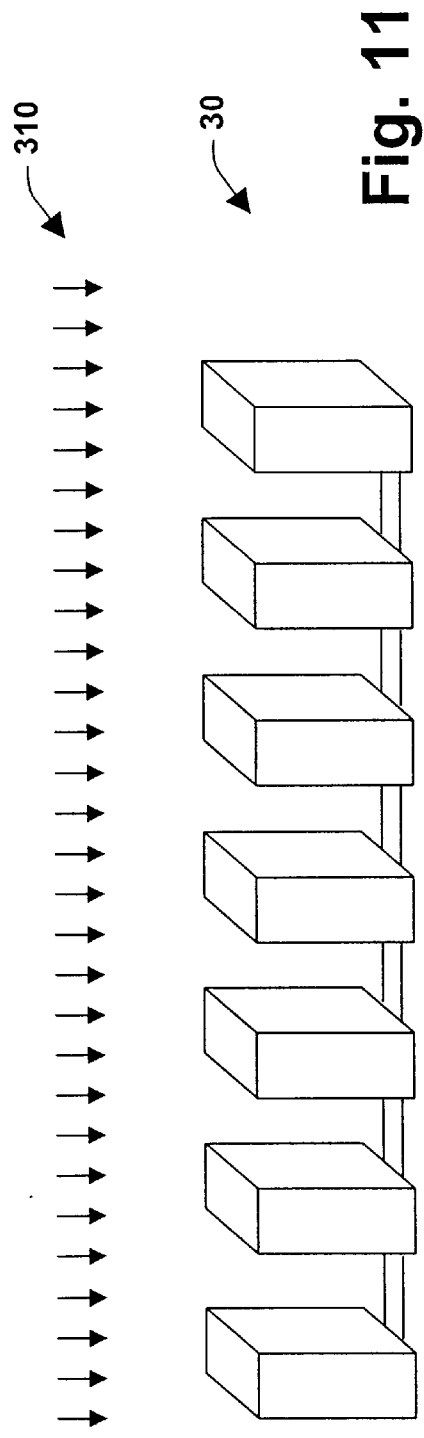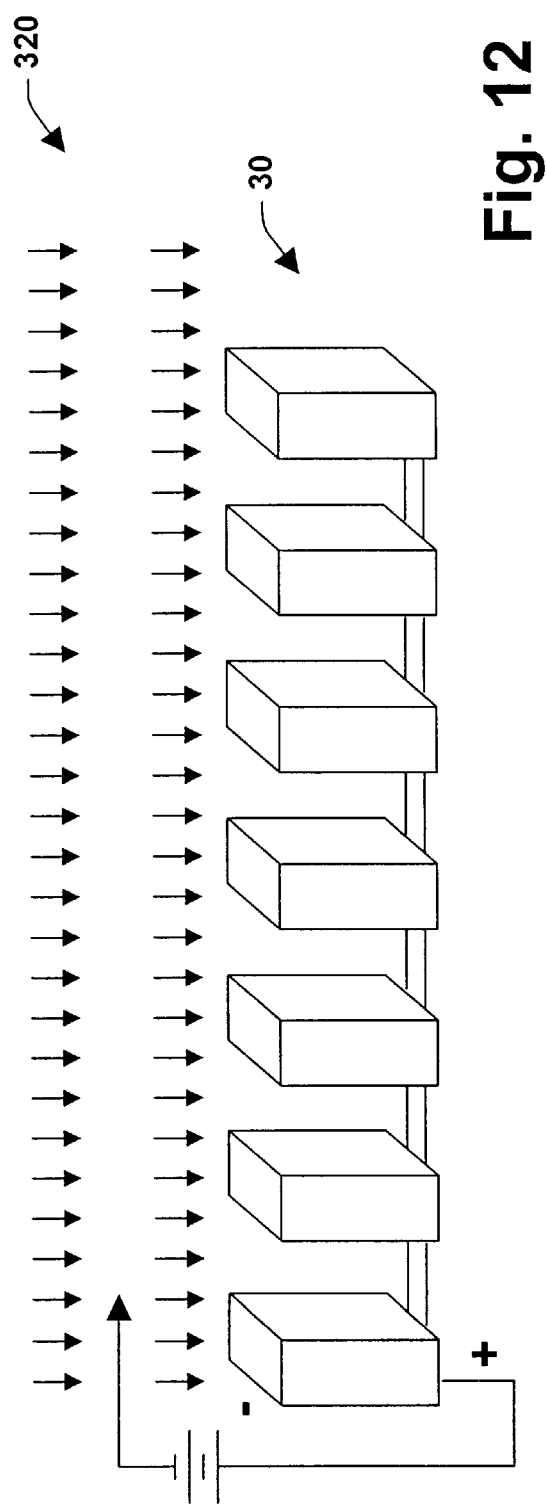

MICRO-VISCOSITY SENSOR AND LUBRICATION ANALYSIS SYSTEM EMPLOYING THE SAME

TECHNICAL FIELD

The present invention generally relates to a micro electromechanical viscosity sensor.

BACKGROUND OF THE INVENTION

Dynamoelectric machines such as motors and generators and other rotating machines such as gears and bearing systems are widely employed in industrial and commercial facilities. These machines are relied upon to operate with minimal attention and provide for long, reliable operation. Many facilities operate several hundreds or even thousands of such machines concurrently, many of which are integrated into a large interdependent process or system. Like most machinery, at least a small percentage of such equipment is prone to failure. Some of such failures can be attributed to loss of lubrication, incorrect lubrication, lubrication breakdown or lubrication contamination.

Depending on the application, the failure of a machine in service can possibly lead to system or process down time, inconvenience, material scrap, hazardous material cleanup and possibly even a dangerous situation. Thus, it is desirable to diagnose the machinery for possible failure or faults early in order to take preventive action and avoid such problems. Absent special monitoring for certain lubrication problems, the problem may have an insidious effect in that although only a minor problem on the onset the problem could become serious if not detected. For example, bearing problems due to inadequate lubrication, lubrication contamination or other causes may not become apparent until irreversible damage has occurred.

Proper lubrication facilitates the extension of machinery life. For example when motor lubrication is continuously exposed to high temperatures, high speeds, stress or loads, and an oxidizing environment, the lubrication will deteriorate and lose its lubricating effectiveness. The loss of lubricating effectiveness will affect two main functions of a lubrication system, namely: (1) to reduce friction; and (2) to remove heat. Continued operation of such a degraded system will result in even greater heat generation and accelerated system degradation. To protect the motor, the lubrication should be changed in a timely fashion. However, a balance must be struck—on one hand it is undesirable to replace an adequate lubricant, but on the other hand it is desired to replace a lubricant that is in its initial stages of breakdown or contamination before equipment damage occurs. Since each particular application of a lubricant is relatively unique with respect to when the lubricant will breakdown or possibly become contaminated, it becomes necessary to monitor the lubricant.

Various techniques for analyzing lubricants are known. For example, measuring a dielectric constant change in the lubricant or recording a thermal history of the lubricant have been employed for monitoring the lubricant's condition. However, these methods require the use of the same lubricant or assume no machinery malfunctions throughout the measurements. Furthermore, these monitoring techniques typically require that a sample of the lubrication be extracted and analyzed using laboratory grade equipment to determine the condition of the lubricant.

Using two-electrode type sensors to measure conductivity changes has been tried. The selectivity of such sensors is generally not sufficient to differentiate between a new lubricant and deteriorated used lubricant. This is because current collected from measuring both new and used lubricants is high. Consequently, it is often difficult for such sensors to distinguish between new and degraded lubricants because all electroactive species are collected with near equal efficiency. Furthermore, it is known that the dielectric constant of different brands of lubricants differ from each other. Therefore, it is difficult to find a dielectric constant value at which all brands of lubricants are definitely bad.

In view of the above, there is a need for an improved sensor for detecting a health condition of a lubricant.

SUMMARY OF THE INVENTION

The present invention relates to a microfabricated viscosity sensor. In particular, the present invention relates to a viscosity sensor of a MEMS (micro-electro mechanical systems) type. The viscosity sensor is made using integrated circuit-like microfabrication techniques (e.g., silicon based fabrication techniques). As a result, the viscosity sensor of the present invention provides for substantial advantages in terms of performance, reduced size, weight and costs—especially since the wafer level technology employed affords for automated and batch production of numerous viscosity sensors on a single wafer.

The viscosity sensor includes a plurality (e.g., array) of finger-like elements (e.g., cilia) which are plated with an electrically conductive material. The finger-like elements extend perpendicularly from the surface of the sensor, and the sensor functions based on the phenomena that a dissipative or damping force that resists the motion of the energized finger-like elements results in an increased power demand to maintain oscillation of the finger-like elements at a particular frequency. A lubricant of high viscosity will exert a greater damping force on the oscillating finger-like elements than a lubricant of lower viscosity. As a result, more power is required to maintain oscillation of the finger-like elements at a particular frequency in a high viscosity lubricant than a lubricant of lower viscosity. Thus, the viscosity of a fluid may be determined via the micro viscosity sensor of the present invention by monitoring the power required to oscillate the finger-like elements at a particular frequency and/or range of frequencies. Since the viscosity of a lubricant is also a function of lubricant temperature (e.g., typically, the higher the lubricant temperature the lower the lubricant viscosity), the present invention also employs a temperature detector to correlate the temperature of the lubricant with the aforementioned power requirements to accurately interpret lubricant viscosity.

The employment of MEMS technology in the fabrication of the viscosity sensor provides for forming a three-dimensional sensor including an array of finger-like elements as compared to a single element. The array of finger-like elements affords increased reliability and sensitivity of the viscosity sensor because of the extended sensing area in contact with the fluid being analyzed. Moreover, the plurality of finger-like elements provides for good resolution of power demand needed to oscillate the finger-like elements at a particular frequency.

Additionally, the viscosity sensor includes a temperature detector for measuring the temperature of the lubricant. Knowledge of the temperature of the lubricant facilitates interpretation of the measured lubricant viscosity. A lubricant analyzer is operatively coupled to the viscosity sensor and provides for determining a health state of the lubricant. The lubricant analyzer employs data (e.g., temperature, oscillation frequency, power draw, voltage signature, current signature) provided by the viscosity sensor to determine the health state of the fluid. More particularly, the data taken alone or in combination will correspond to a particular viscosity and/or health state of the lubricant. The lubricant analyzer compares a current set of data to a known set of historical and normative data relating to the condition of the lubricant in order to assess the present condition of the lubricant.

In accordance with one aspect of the present invention, a micro-viscosity sensor for sensing the viscosity of a fluid includes at least one sensing element exposed to the fluid, the at least one sensing element adapted to be oscillated over a range of frequencies; wherein the viscosity of the fluid is determined as a function of the power required to maintain oscillation of the at least one sensing element at a predetermined frequency.

In accordance with another aspect of the present invention, a lubricant analysis system includes at least one micro-viscosity sensor which includes an array of finger-like elements extending perpendicular to the surface of a semiconductor base, the array of finger-like elements being oscillated at a predetermined frequency, wherein the power required to maintain oscillation of the array of finger-like elements at the pre-determined frequency corresponds to the viscosity of the fluid. The system also includes a lubrication analyzer which includes a processor operatively coupled to the at least one micro-viscosity sensor, the processor adapted to process data output from the at least one micro-viscosity sensor to determine the viscosity of the fluid.

Another aspect of the present invention relates to a method for fabricating a micro-viscosity sensor, including etching a semiconductor substrate to form an array of finger-like elements which extend perpendicularly from a base of the substrate, the array of finger-like elements adapted to oscillate over a range of frequencies, wherein the power required to maintain oscillation of the array of finger-like elements at a particular frequency corresponds to the viscosity of a fluid being sensed.

Yet another aspect of the present invention provides for a micro-viscosity sensor for measuring the viscosity of a lubricant including at least one finger-like element extending from the surface of a semiconductor base, the at least one finger-like element operative to be oscillated over a range of frequencies. The micro-viscosity also includes a temperature detector, wherein the conductivity of the temperature detector varies in correspondence with the temperature of the lubricant. A first set of electrical contacts provides electrical connection to the at least one finger-like element; and a second set of electrical contacts provides electrical connection to the temperature detector.

Another aspect of the present invention is a method for sensing the viscosity of a fluid including the steps of: oscillating at least one element extending from the surface of a semiconductor base, the at least one element operative to be oscillated over a range of frequencies; using a temperature detector to measure the temperature of the fluid, wherein the conductivity of the temperature detector varies in correspondence with the temperature of the lubricant; and determining the power required to maintain oscillation of the at least one element at a particular frequency, the particular frequency being different than a natural resonant frequency of the at least one element, wherein the power required is a function of the viscosity of the fluid.

Still another aspect of the present invention provides for a viscosity sensing system which includes at least one micro-viscosity sensor. The micro-viscosity sensor includes an array of elements extending from the surface of a semiconductor base, the array of elements being oscillated at a pre-determined frequency, wherein the power required to maintain oscillation of the array of finger-like elements at the pre-determined frequency corresponds to the viscosity of the fluid. The viscosity sensing system also includes a lubrication analyzer including a processor operatively coupled to the at least one micro-viscosity sensor, the processor adapted to process data output from the at least one micro-viscosity sensor to determine the viscosity of the fluid. The integrated viscosity sensing system provides for in situ monitoring of the fluid.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 4a is a graphical illustration of an input signal for oscillating an array of finger-like elements in a high viscosity fluid in accordance with one embodiment of the present invention;

FIG. 4b is a graphical illustration of an input signal for oscillating an array of finger-like elements in a low viscosity fluid in accordance with one embodiment of the present invention;

FIG. 4c is a graphical illustration of a control signal and an output signal from a viscosity sensor exposed to a high viscosity lubricant in accordance with one embodiment of the present invention;

FIG. 5a is a table diagram of viscosity sensor input signal signatures over a range of temperatures and frequencies, which may be used to facilitate diagnosing the health state of a lubricant in accordance with one embodiment of the present invention;

FIG. 5b is a representative table diagram of fluid viscosity health states based upon actual power requirements to maintain oscillation of an array of finger-like elements at a particular frequency at particular temperatures;

FIG. 6a is a functional schematic diagram a motor bearing lubricant diagnostic system in accordance with one embodiment of the present invention;

FIG. 6c is a functional schematic diagram of a lubricant diagnostic system for diagnosing the viscosity of lubricants for a plurality of machines in accordance with another embodiment of the present invention;

FIG. 11 is a perspective illustration of the array of finger-like elements of FIG. 10 being seeded with a seed material in accordance with one embodiment of the present invention;

FIG. 12 is a perspective illustration of the array of finger-like elements of FIG. 11 being plated with an inert conductive material in accordance with one embodiment of the present invention;

DETAILED DESCRIPTION OF THE INVENTION

Figure 1:
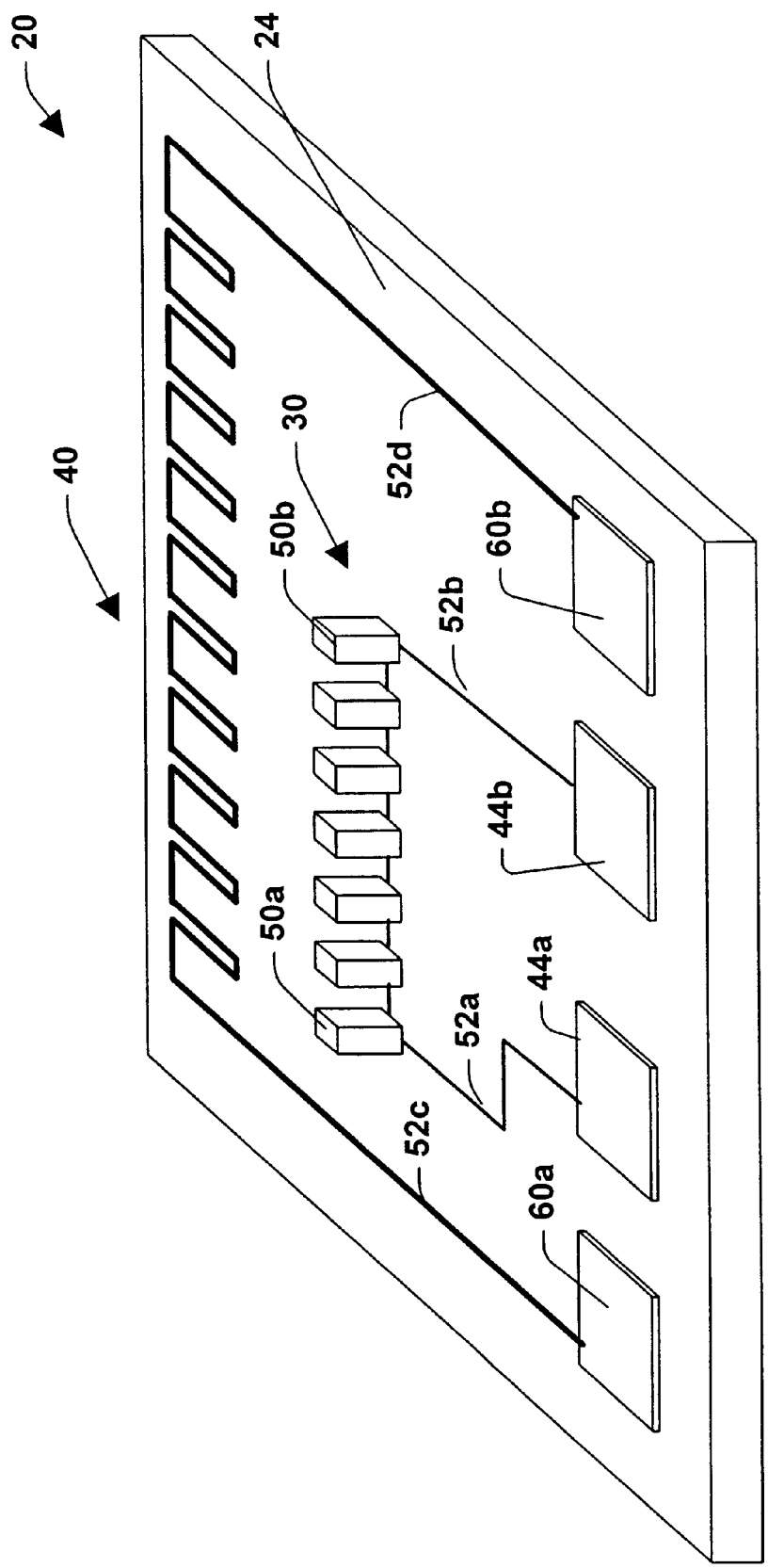
FIG. 1 is a perspective illustration of a viscosity sensor in accordance with one embodiment of the present invention.

The present invention will now be described with reference to the drawings, wherein like reference numerals are used to refer to like elements throughout.

As is mentioned above, the present invention relates to a MEMS-type viscosity sensor which includes a plurality of finger-like elements (e.g., cilia). The plurality of finger-like elements are oscillated at a fixed frequency, and the power required to drive such oscillation corresponds to the viscosity of a lubricant the sensor is in contact with.

Referring initially to FIG. 1 an exemplary viscosity sensor 20 in accordance with the present invention is shown in perspective view. The viscosity sensor 20 includes a semi-conductor base 24 which preferably comprises silicon, however, any suitable material may be employed. Protruding perpendicularly from the base 24 is an array of finger-like elements 30 which may be the same material as the base 24. As will be discussed in greater detail below, the base 24 and the array of finger-like elements 30 are formed by etching a semiconductor substrate material. The array of finger-like elements 30 are designed to extend into and be coated by the lubricant that is being measured. The finger-like elements 30 will be damped by the lubricant as a function of the viscosity of the lubricant. Accordingly, such damping effect will influence the amount of power required to oscillate the finger-like elements 30 at a desired frequency.

The lubricant creates a dissipative or damping force that resists the motion of the energized finger-like elements. Thus, the higher the viscosity of the lubricant the more power that is required to oscillate the finger-like elements at a particular frequency. As will be discussed in greater detail below, by monitoring the power required to oscillate the finger-like elements at a particular frequency, the particular frequency being different than a natural resonant frequency of the finger-like elements, and employing other interpretive parameters (e.g., temperature) the viscosity and/or health state of the lubricant can be determined.

The viscosity sensor 20 includes a temperature detector 40 located on the surface of the base 24. The temperature detector 40 is preferably formed from platinum, however, it is to be appreciated that any material (e.g., gold) suitable for carrying out the present invention may be employed. The temperature detector 40 is patterned on the base in accordance with a predetermined length, width and surface area. Therefore, by knowing the surface area of the temperature detector and the material of which it is made, a temperature of a lubricant to which the temperature sensor 40 is exposed may be determined based on the electrical conductivity of the temperature detector 40. Knowledge of the lubricant temperature is useful in interpreting the viscosity of the lubricant being analyzed because lubricant viscosity is a function of lubricant temperature. In general, the higher is the lubricant temperature, the lower is the lubricant viscosity. However, some lubrication problems (e.g., water contamination) may result in a different lubricant viscosity at the measured temperature than the viscosity expected in fresh, healthy lubrication. The present invention correlates lubricant temperature with the power required to oscillate the array of finger-like elements 30 at a desired frequency to establish the health of the lubrication.

A set of electrical contacts 44a and 44b are patterned on the base 24 and are bonded to a conductive plating (FIGS. 11–12) coating and connect the array of finger-like elements 30 via conductive pathways 52. In particular, the array of finger-like elements 30 are plated (e.g., electroplated) with an inert conductive material such as nickel or the like. The plating serves to electrically couple each of the finger-like elements to one another. The electrical contacts 44a and 44b provide for electrical connection to the array of finger-like elements 30 for oscillating the finger-like elements at a desired frequency. Electrical contact 44a is coupled to a finger-like element 50a at one end of the array 30 via a conductor 52a. Electrical contact 44b is coupled to a finger-like element 50b at the other end of the array 30 via a conductor 52b.

Another set of electrical contacts 60a and 60b patterned on the base are coupled via the conductive pathways 52c and 52d to the temperature detector 40.

The viscosity sensor 20 is small having a square area of approximately 4 mm. Accordingly, the viscosity sensor 20 is desirable for use in applications where space is at a premium but where accuracy, reliability, and sensitivity of measured data are also at a premium. Furthermore, because the viscosity sensor 20 is fabricated in accordance with integrated circuit-like fabrication techniques, large batches of the sensors 20 may be easily and efficiently produced with good production yields.

Figure 13:
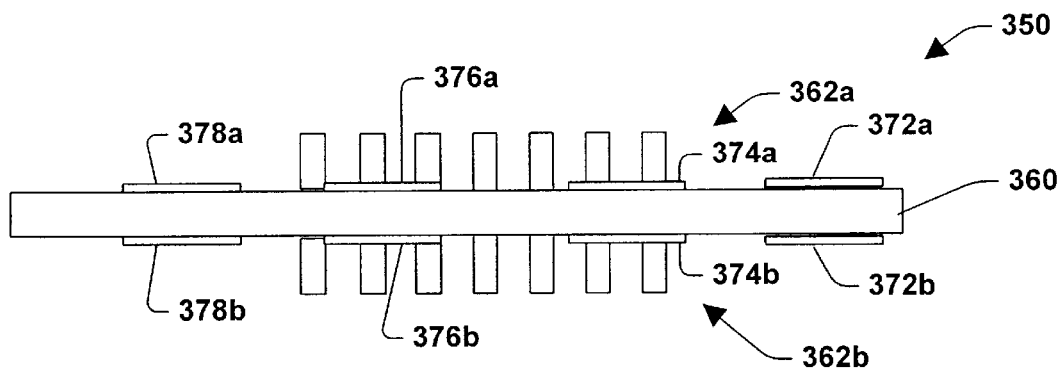
FIG. 13 is a front view of a viscosity sensor in accordance with another embodiment of the present invention.

It is to be appreciated that a mirror set of temperature detector, array of finger-like elements and electrical contacts may be formed on the other side of the base 24 so as to increase the functionality of the viscosity sensor 20 (See FIG. 13).

Figure 2:
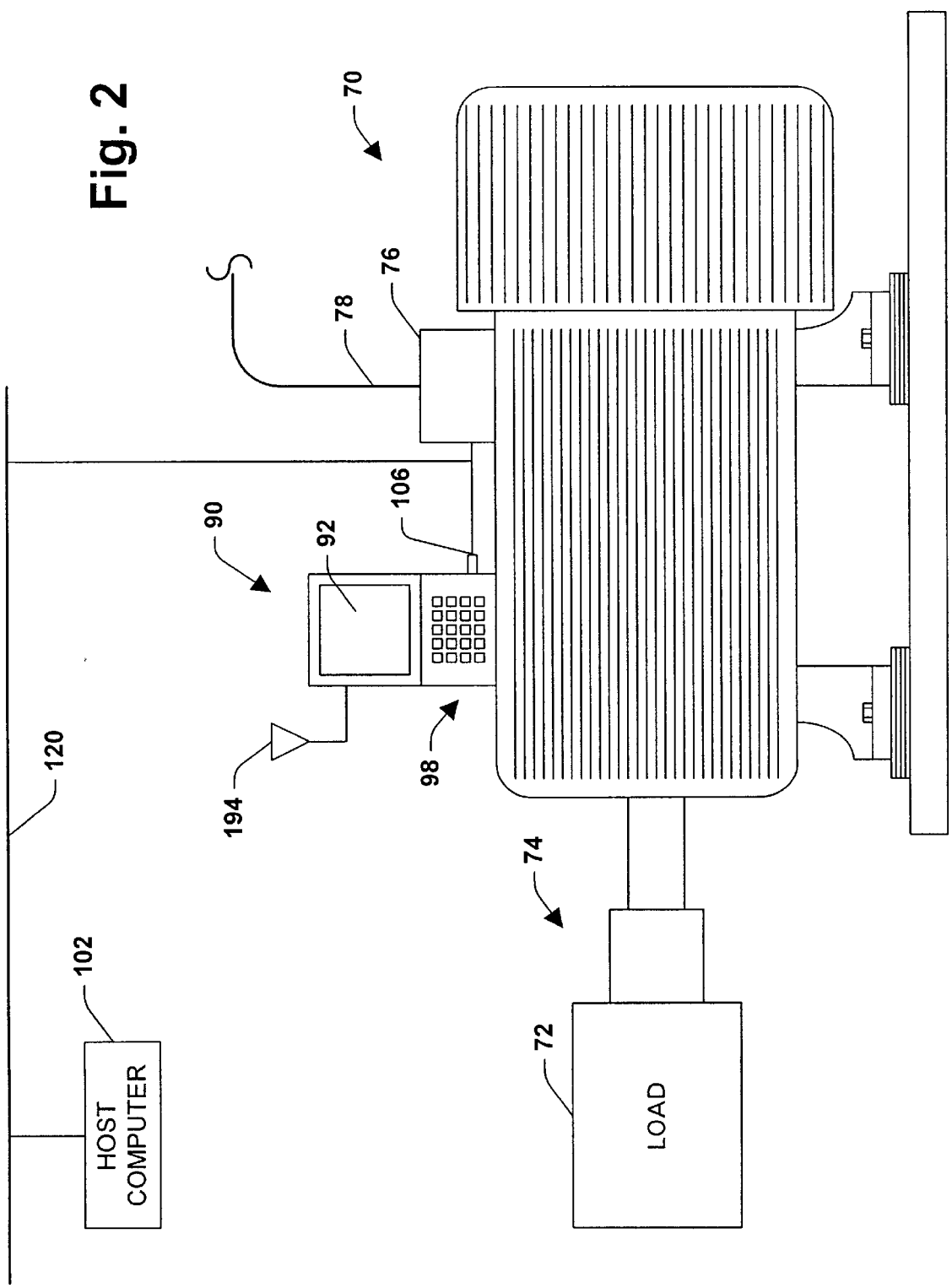
FIG. 2 is a functional schematic diagram of an integrated AC induction motor and lubricant analyzer employing the viscosity sensor of FIG. 1 in accordance with one embodiment of the present invention.

Turning now to FIG. 2, an exemplary environment in which the present invention may be employed is shown. A three-phase AC induction motor 70 is depicted driving a load 72 through a shaft coupling 74. The motor 70 includes a junction box 76 for receiving conductors from power lines via a conduit 78, which are tied to power supply lines (not shown) of the motor 70. The motor 70 is AC powered and operates at an AC power line frequency of 60 Hz. However, it is appreciated that different line frequencies (e.g., 50 Hz) may be employed. Coupled to the motor 70 is a lubricant analyzer 90 (FIG. 3) which as will be discussed in greater detail below provides for receiving and processing data relating to the health of lubricant employed by the motor 70.

The lubricant analyzer 90 includes a display 92 for displaying to an operator information relating to the health of the lubricant. It is to be appreciated that the lubricant analyzer 90 may also perform other functions relating to determining the health of the motor 70 (e.g., current signature analysis, vibration analysis, etc.). The lubricant analyzer 90 further includes an operator input device 98 in the form of a key pad which enables a user to enter data, information, function commands, etc. as is conventional. For example, the user may input information relating to lubricant type via the keypad 98 for subsequent transmission to a host computer 102. In addition, the keypad 98 may include up and down cursor keys for controlling a cursor which may be shown on the display 92. The lubricant analyzer 90 includes a communications port 106 for interfacing the lubricant analyzer 90 with the viscosity sensor 20 (FIG. 3) and the host computer 102 via a suitable communications link.

According to an embodiment of the present invention, the lubricant analyzer 90 is part of a communication system including a network backbone 120. The network backbone 120 may be a hardwired data communication path made of twisted pair cable, shielded coaxial cable or fiber optic cable, for example, or may be wireless or partially wireless in nature. Information is transmitted via the network backbone 120 between the host computer 102 and the lubricant analyzer 90. The communication link preferably adheres to the RS232C or DeviceNet standard for communicating command and parameter information. However, any communication link suitable for carrying out the present invention may be employed.

Figure 3:
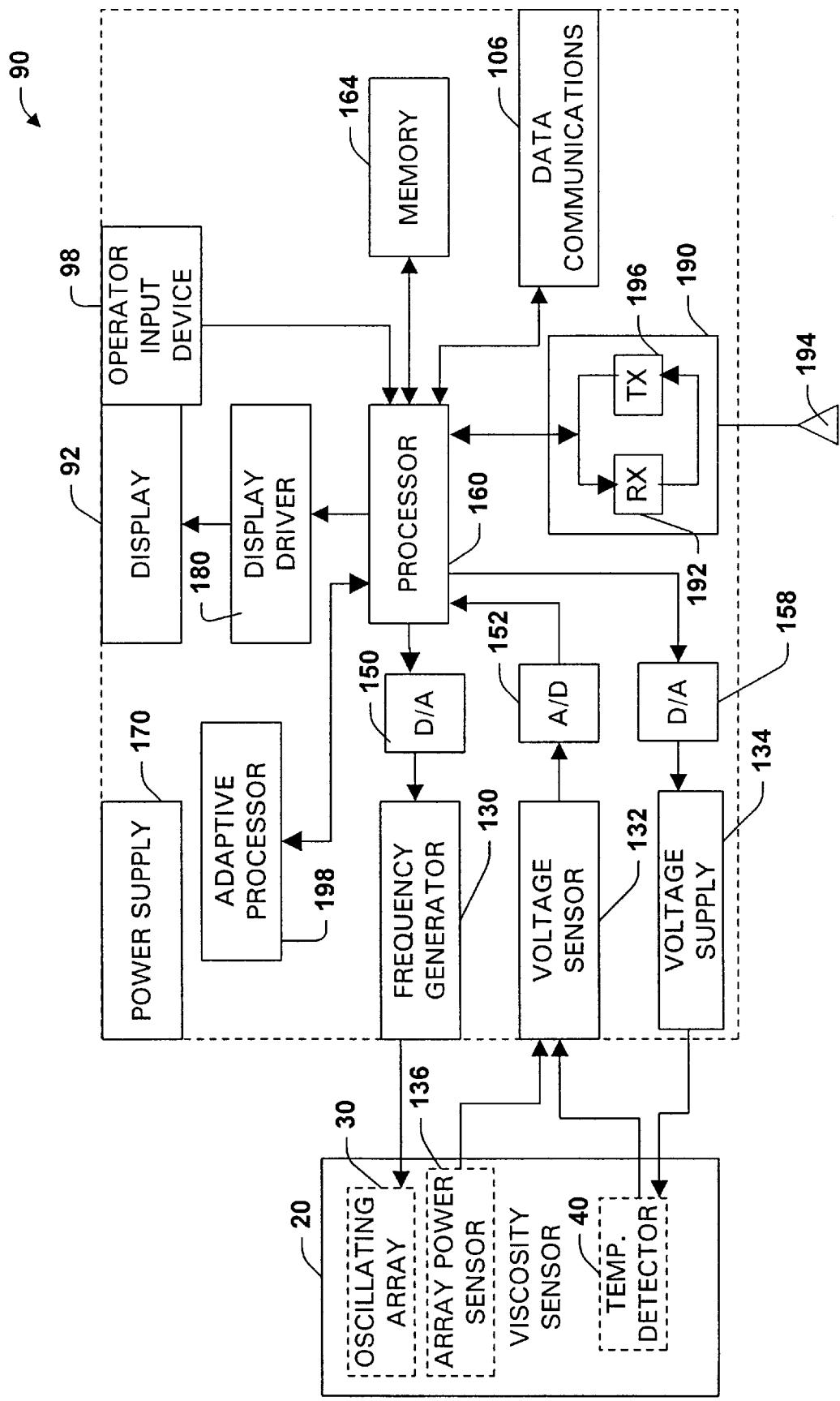
FIG. 3 is a block diagram of a viscosity sensor and lubricant analyzer in accordance with one embodiment of the present invention.

Referring now in particular to FIG. 3, a schematic representation of the present invention is shown according to one particular aspect of the present invention, wherein the lubricant analyzer 90 is integrated with the viscosity sensor 20. However, it will be appreciated from the discussion herein that the lubricant analyzer 90 may be located remotely from the motor 70. Furthermore, it is to be appreciated that the host computer may serve to carry out substantially all of the functions described herein performed by the lubricant analyzer 90. It is also to be appreciated that in accordance with another specific aspect of the present invention, the lubricant analyzer 90 (absent certain components) may be integrated onto a semiconductor chip with the viscosity sensor 20. In accordance with another specific embodiment, the lubricant analyzer 90 may be completely integrated within the motor 70 (e.g., in an intelligent motor).

In the preferred embodiment, the lubricant analyzer 90 includes a housing which is suitably shielded to protect the lubricant analyzer 90 from whatever environment (e.g., dust, moisture, heat, vibration, lubrication) the motor 70 is working in. Additionally, the interior of the lubricant analyzer 90 may be suitably insulated with thermal insulation so as to protect it from heat generated by the motor 70.

The viscosity sensor 20 is coupled to a frequency generator (e.g., oscillator) 130, voltage sensor 132 and voltage supply 134 of the lubricant analyzer 90. In particular, the frequency generator 130 is operatively coupled to the array of finger-like elements 30, and the voltage sensor 132 is operatively coupled to an array power sensor 136. The array power sensor 136 measures the amount of power required to maintain oscillation of the array at a particular frequency. The temperature detector 40 is coupled to the voltage supply 134 and voltage sensor 132. The frequency generator 130 is preferably sufficiently stable and accurate so as to be adjustable to oscillate the array of finger-like elements 30 over a range of frequencies defined in air and in the most viscous lubricant to be measured. As noted above, power required to oscillate the array 30 at a desired frequency will depend on the state (e.g., viscosity, contamination state) of the lubricant.

The temperature detector 40 varies in electrical conductivity depending on the temperature of the lubricant. Accordingly, the temperature of the lubricant can be determined from the output of the voltage sensor 132 which is coupled to the temperature detector 40 because the output voltage will vary in correspondence with the lubricant temperature. The following table illustrates the analytic relationship between lubricant viscosity and lubricant temperature, which can be monitored via the conductivity of the temperature detector 40.

| CONDUCTIVITY OF TEMP. DETECTOR 40 | LUBRICANT TEMPERATURE | GOOD LUBRICANT VISCOSITY |
| --- | --- | --- |
| $V_1$ | $T_1$ | $LV_1$ |
| $V_2$ | $T_2$ | $LV_2$ |
| $V_3$ | $T_3$ | $LV_3$ |
| . | . | . |
| . | . | . |
| $V_N$ | $T_N$ | $LV_N$ |

The frequency generator 130 and voltage sensor 132 are tied to digital-to-analog (D/A) and analog-to-digital (A/D) converters 150 and 152 respectively of the lubricant analyzer 90. The analog-to-digital converter 152 provides a processor 160 with digitally converted signals corresponding to the analog measurements collected by the viscosity sensor 20. The voltage supply 134 is also tied to the processor 160 via a D/A converter 158. The viscosity sensor 20 may be tailored to output measurements in any suitable format in accordance with the present invention. For example, the output signals may be provided as digital-serial; digital parallel; or current (4–20 mA).

The processor 160 is responsible for controlling the general operation of the lubricant analyzer 90. The processor 160 is programmed to control and to operate the various components of the lubricant analyzer 90 in order to carry out the various functions described herein. The processor or CPU 160 can be any of a plurality of suitable processors, such as the p24T, Pentium 50/75, Pentium 60/90, and Pentium 66/100, Pentium PRO and Pentium 2, and other similar and compatible processors. The manner in which the processor 160 can be programmed to carry out the functions relating to the present invention will be readily apparent to those having ordinary skill in the art based on the description provided herein and thus further discussion related thereto is omitted for sake of brevity.

A memory 164 tied to the processor 160 is also included in the lubricant analyzer 90 and serves to store program code executed by the processor 160 for carrying out operating functions of the lubricant analyzer 90 as described herein.

The memory 164 also serves as a storage medium for storing information such as nominal lubricant temperature and viscosity data, lubricant viscosity tables (FIGS. 5a and 5b), oscillator control information, and the like. The memory 164 may also include machine specific data and acceptable error bounds/deviation values which may be used to facilitate determining the suitability of the lubricant being analyzed. The memory may also be used to store current and historical viscosity and temperature values. The data may be transmitted to a central processor and/or employed to perform time-based trending and analysis to determine lubricant health.

The memory 164 includes read only memory (ROM) and random access memory (RAM). The ROM contains among other code the Basic Input-Output System (BIOS) which controls the basic hardware operations of the lubricant analyzer 90. The RAM is the main memory into which the operating system and application programs are loaded. The memory 164 is adapted to store a complete set of the information to be displayed. According to a preferred embodiment, the memory 164 has sufficient capacity to store multiple sets of information, and the processor 160 could include a program for alternating or cycling between various sets of display information. This feature enables the display 92 to show a variety of effects conducive for quickly conveying lubricant state information to a user.

Power is provided to the processor 160 and other components forming the lubricant analyzer 90 from a power supply 170.

The lubricant analyzer 90 includes a data communication system which includes a data communication port 106 and communications card (not shown), which is employed to interface the processor 160 with the host computer 102 via the network 120 (FIG. 2). The communication link preferably adheres to the RS232C or DeviceNet standard for communicating command and parameter information. However, any communication link suitable for carrying out the present invention may be employed.

It should be appreciated that the present invention may be used in a system which does not include the host computer 102. All processing including data analyses and lubricant state estimation and health determination could be accomplished by the processor 160 and the results transmitted to a PC or a control computer such as a programmable logic controller (PLC) (not shown). Furthermore, only one data link may be required. According to another embodiment, the processor 160 could be employed to simply trigger a single bit, digital output which may be used to open a relay and turn the motor 70 off.

The display 92 is coupled to the processor 160 via a display driver circuit 180 as is conventional. The display 92 may be a liquid crystal display (LCD) or the like. In the preferred embodiment, the display 92 is a fine pitch liquid crystal display operated as a standard CGA display with a resolution of 640×200 pixels. The display 92 functions to display data or other information relating to the state of the lubricant and if desired the state of the motor 70. For example, the display 92 may display a set of discrete lubricant condition indicia such as, for example, temperature, viscosity, and normal operation indicia which is displayed to the operator and may be transmitted over the network 120. The display 92 is capable of displaying both alphanumeric and graphical characters.

Alternatively, the display 92 may comprise one or more light emitting diodes (LEDs) (e.g., a tri-color LED displaying green, yellow or red colors depending on the health state of the lubricant).

The lubricant analyzer 90 also includes its own RF section 190 connected to the processor 160. The RF section 190 includes an RF receiver 192 which receives RF transmissions from the host computer 102 for example via an antenna 194 and demodulates the signal to obtain digital information modulated therein. The RF section 190 also includes an RF transmitter 196 for transmitting information via a wireless link to the host computer 102 for example in response to an operator input.

Referring briefly to FIGS. 4a-4c, representative graphs of electrical signals are shown with respect to determining lubricant viscosity in accordance with the present invention. The signals of FIGS. 4a and 4b are signals employed to drive the array of finger-like elements 30 at a particular frequency in a high viscosity lubricant (FIG. 4a) and a low viscosity lubricant (FIG. 4b). As can be seen, the amplitude (corresponding to power requirements) is higher for the high viscosity fluid than the low viscosity fluid. Thus, more power is required to oscillate the array of finger-like elements at the particular frequency in the high viscosity fluid as compared to the low viscosity fluid.

FIG. 4c illustrates another embodiment of the present invention wherein instead of maintaining oscillation of the array of finger-like elements at a desired frequency, the array 30 is energized to oscillate and then such energization is ceased. The oscillation of the array 30 will decay faster in a high viscosity fluid than a low viscosity fluid because of the greater damping forces associated with high viscosity fluids. Accordingly, the lubricant analyzer 90 can measure the rate of such oscillation decay, correlated with fluid temperature to determine the viscosity of the fluid.

Fast Fourier Transforms (FFTs) of the output signals of FIGS. 4a-4c may be utilized to readily perform signature analysis. The processor 160 may control the signal sampling and digitizing rate as well as any buffering of the digitized output signals that might be needed. The data collection rate may be carried out at for example 26,203 samples per second over a period of 2 seconds. This data collection rate provides sufficient data upon which the processor 160 can generate a comprehensive frequency spectrum of the output signals suitable for analysis using commercially available Fast Fourier Transform software such as for example MAT-LAB by The Math Works. The FFTs of the output signal data may be discretized over N number of points for ease of processing. In the preferred embodiment, N=2,048, however, it will be appreciated that the FFTs of each signal may be discretized over any suitable number of points.

Returning back to FIG. 3, the lubricant analyzer 90 may also include an adaptive processor 198 such as for example a neural network or an expert system to facilitate analyzing the health state of the lubricant. Alternatively, the adaptive processor 90 may be located in the host computer 102 if desired.

The programming or training of neural networks involves supplying the input and corresponding output data of samples containing features, similar to those being searched for. The neural network in turn learns by adjusting weights assigned to each of the neurons. The weights and threshold values of the neurons determine the propagation of data through the network and thus provides a desired output based on a respective set of inputs.

Expert systems are knowledge-based systems which are typically rule-based. An expert system is employed in accordance with the present invention by establishing a hardware or software based program which contains encoded domain knowledge from a knowledge expert as to the relationship between items of information being sought for classification in this case lubricant state. That is, the expert system codifies expert knowledge as a rule or set of rules for each decision and stores given rules and data into the knowledge base. The expert system will typically employ an "inference" engine to derive health-related knowledge about the subject.

Once the processor 160 has processed all of the respective lubricant data, the processed data may be sent to the host computer 102 for subsequent analysis and trending. The host computer 102 may then make determinations as to the health of the lubricant based on the data received from the lubricant analyzer 90. Accordingly, lubricant maintenance can be scheduled to correspond with the state of the lubricant. Additionally, the processed data can be compiled for trend analysis and forecasting. Since the lubricant analyzer 90 is integrated with the motor 70, the data sampling rate can be substantially high thus providing for improved highly accurate and up to date data relating to the health of the lubricant.

However, as mentioned above, it is to be appreciated that lubricant diagnosis, trend analysis, forecasting, etc. that could be performed by the host computer 102 may also be performed directly by the lubricant analyzer 90. For example, turning now to FIG. 5*a* a table 200 is shown which the processor 160 may access when performing analyses to diagnose the state of the lubricant. The table 200 includes input signal amplitude data ($A_0$ thru $A_z$) corresponding to power requirements to maintain oscillation of the array of finger-like elements 30 over a range of frequencies ($f_0$ thru $f_N$) and temperatures ($TEMP_1$, thru $TEMP_N$), and good fluid viscosity values ($V_0$ thru $V_z$) corresponding to the amplitude data. Although not shown for ease of understanding, it is to be appreciated that the table may also include correlation to other lubricant parameters. The table 200 is stored in the memory 164 of the lubricant analyzer 90 so as to be easily accessible by the processor 160. The table 200 includes various good health states of the lubricant which correspond to input signal amplitudes over the frequency range $f_0$ thru $f_N$ and temperatures ($TEMP_1$ thru $TEMP_N$). As will be appreciated, the table 200 can store an enormous amount of the input signal signatures corresponding to various health states of the lubricant, which the processor 160 can employ to diagnose the state of the lubricant.

FIG. 5*b* is a representative table diagram 210 of fluid viscosity health states based upon actual power requirements to maintain oscillation of the array of finger-like elements 30 at a particular frequency at particular temperatures. The table 210 lists actual fluid viscosity related data in connection with one specific frequency (e.g., $f_1$). It is to be appreciated that many similar tables exist for each particular frequency of the range of frequencies ($f_O$–$f_N$) (see table 200). Although the table 210 only shows ranges of good fluid viscosity and bad fluid viscosity for ease of understanding, it is to be appreciated that specific numeric viscosity values for every particular combination of power requirement and temperature may be stored in the table 210.

Turning now to FIG. 6*a*, a lubricant analysis system 250 in accordance with an embodiment of the present invention is shown. In this embodiment, it is desired to monitor the state of a lubricant 256 employed to lubricate a motor bearing 258. As shown, the viscosity sensor 20 is located proximate to the motor bearing 258 and is in contact with the bearing lubricant 256. The viscosity sensor 20 is also coupled to the lubricant analyzer 90 which receives and processes data gathered by the viscosity sensor in the manner described above.

In many motor designs, and particularly in motor designs utilizing spherical or self-aligning bearings, the use of unsuitable lubrication (degraded, contaminated, etc.) prevents maintaining a suitable lubrication film between the bearing and the bearing raceway so as to minimize wear and heating of the bearing. In turn, this inadequate lubrication oftentimes results in excessive friction, wear, and heat, which in turn may cause premature failure of the bearing thus possibly resulting in detrimental effects on the health and efficiency of the motor.

The present invention affords for monitoring the health of the bearing lubricant in a precise, reliable, inexpensive, convenient and substantially continuous manner. The lubricant analysis system 250 provides for frequently monitoring the health state of the lubricant 256, and can provide for scheduled maintenance of the lubricant 256 in order to facilitate maximizing the life and efficiency of the motor bearing 258 and minimizing maintenance cost.

It is to be appreciated that the present invention has numerous applications (e.g., forced lubrication systems; gear boxes; hydrodynamic bearings and other bearing systems, oils, grease, hydraulic fluids, cutting oils and other types of fluids where knowledge of the viscosity thereof is desired). Each are susceptible to problems and exhibit symptoms with viscosity and temperature as described here (e.g. contamination, breakdown). All such applications are intended to fall within the scope of the present invention as defined in the claims.

Figure 6B:
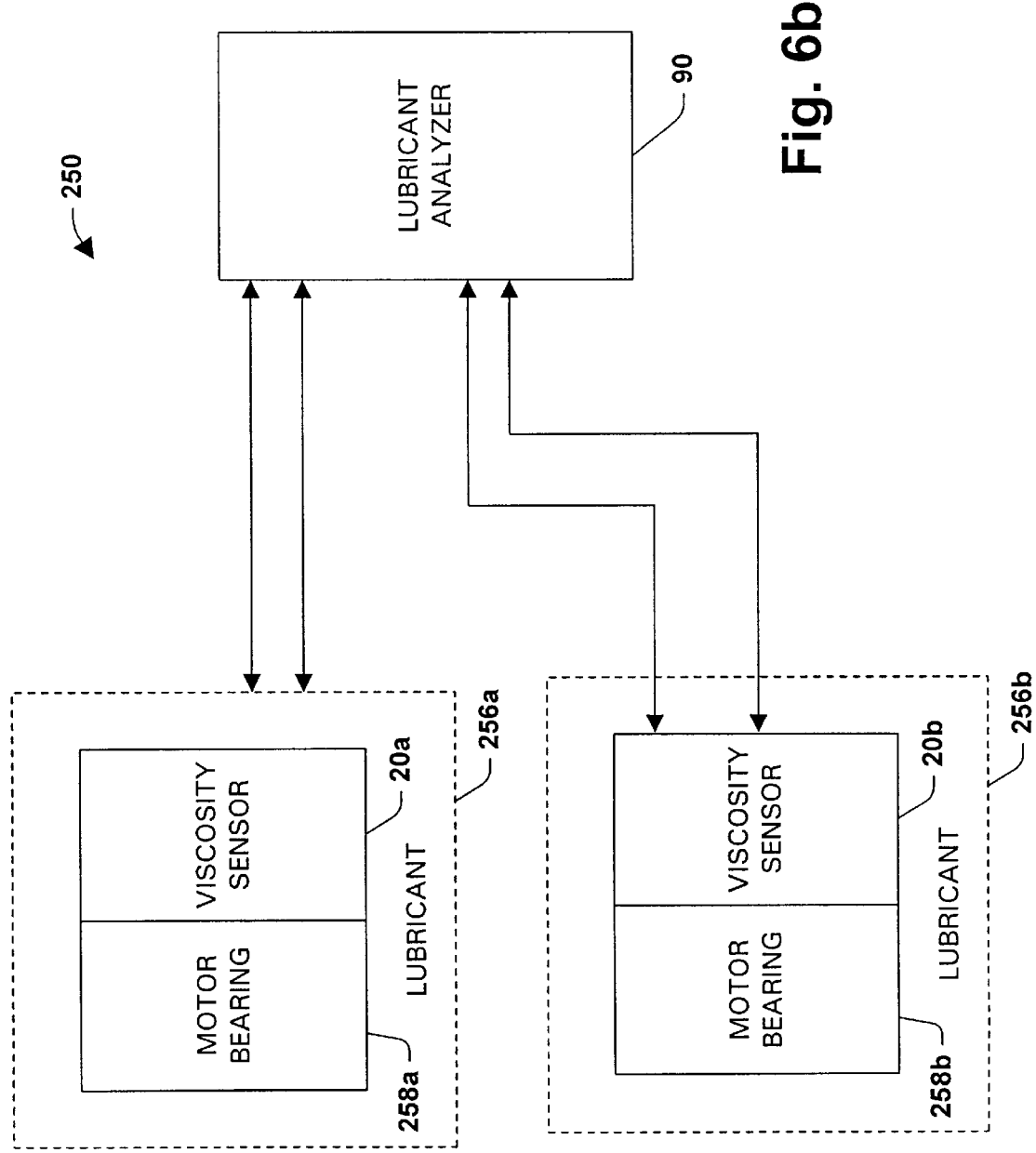
FIG. 6b is a functional schematic diagram of a motor bearing lubricant diagnostic system in accordance with another embodiment of the present invention.

FIG. 6*b* illustrates another aspect of the present invention wherein the lubricant analyzer 90 is coupled to two different viscosity sensors $20_a$ and $20_b$. Viscosity sensor $20_a$ is coupled to a load end bearing $258_a$, and viscosity sensor $20_b$ is coupled to a fan end bearing $258_b$. The lubricant analyzer 90 will monitor the health states of lubricants $256_a$ and $256_b$ for each respective bearing.

It is to be appreciated that a plurality of viscosity sensors ($20_1$ thru $20_n$) may be coupled to a single lubricant analyzer 90 as shown in FIG. 6*c*. Thus, the health state of lubricants of several different pieces of equipment (e.g., motors, gear box, pillow block, pump) may be monitored by the lubricant analyzer 90.

Figure 7:
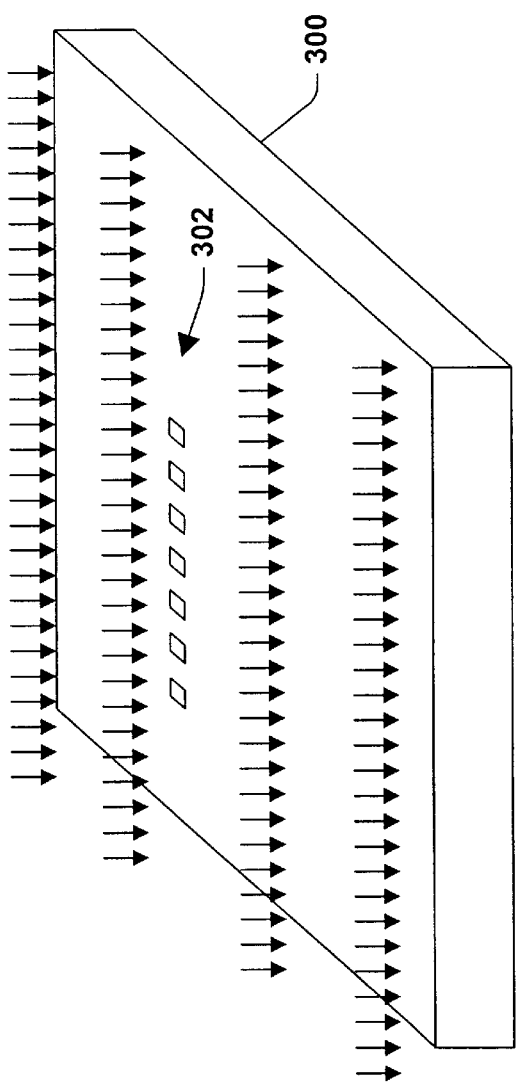
FIG. 7 is a perspective illustration of a silicon substrate being etched to form an array of finger-like elements in accordance with one embodiment of the present invention.

Turning now to FIGS. 7–12, an exemplary batch fabrication methodology for the viscosity sensor 20 is provided. Referring now to FIG. 7 in particular, the process begins with a substrate layer 300 of semiconductor material such as silicon for example, but it is to be appreciated that any suitable material for carrying out the present invention may be employed. An initial patterning step is performed wherein via employment of a suitable photoetch portions of the substrate which are later to become an array of finger-like elements are patterned and masked (via a photo resist). The unmasked portions of the substrate 300 are etched (e.g., via suitable chemical etching or reactive ion beam etching). Preferably, the etching is performed using reactive ion beam etching (e.g., via Argon) because it is a substantially dry etching methodology and provides for suitably deep etching of the substrate 300. Suitable ion implantation and energy levels are employed for carrying out the present invention.

If wet etching is desired, the bottom side of the substrate 300 may be doped with Boron to form an etch stopper of a desired thickness which will facilitate stopping the wet etch at a desired depth.

Figure 8:
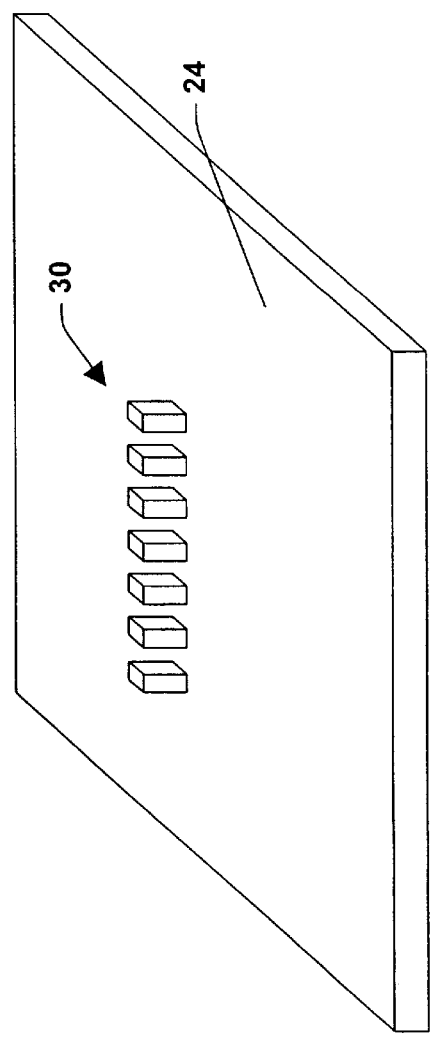
FIG. 8 is a perspective illustration of the silicon substrate of FIG. 7 after the etching step to form an array of finger-like elements in accordance with one embodiment of the present invention.

FIG. 8 illustrates the array of finger-like elements 30 that result after the substrate 300 has been etched and the first mask stripped away. The remaining planar area of the substrate 300 serves as the base 24 of the viscosity sensor 20. In the preferred embodiment, the base has a width of about 2 mm, and each finger in the array of finger-like elements 30 have a height of about 1–2 microns and a width of about 0.1–0.5 microns. It is to be appreciated that the base area and array height and width may be tailored to any dimensions suitable for carrying out the present invention with respect to a particular application.

Figure 9:
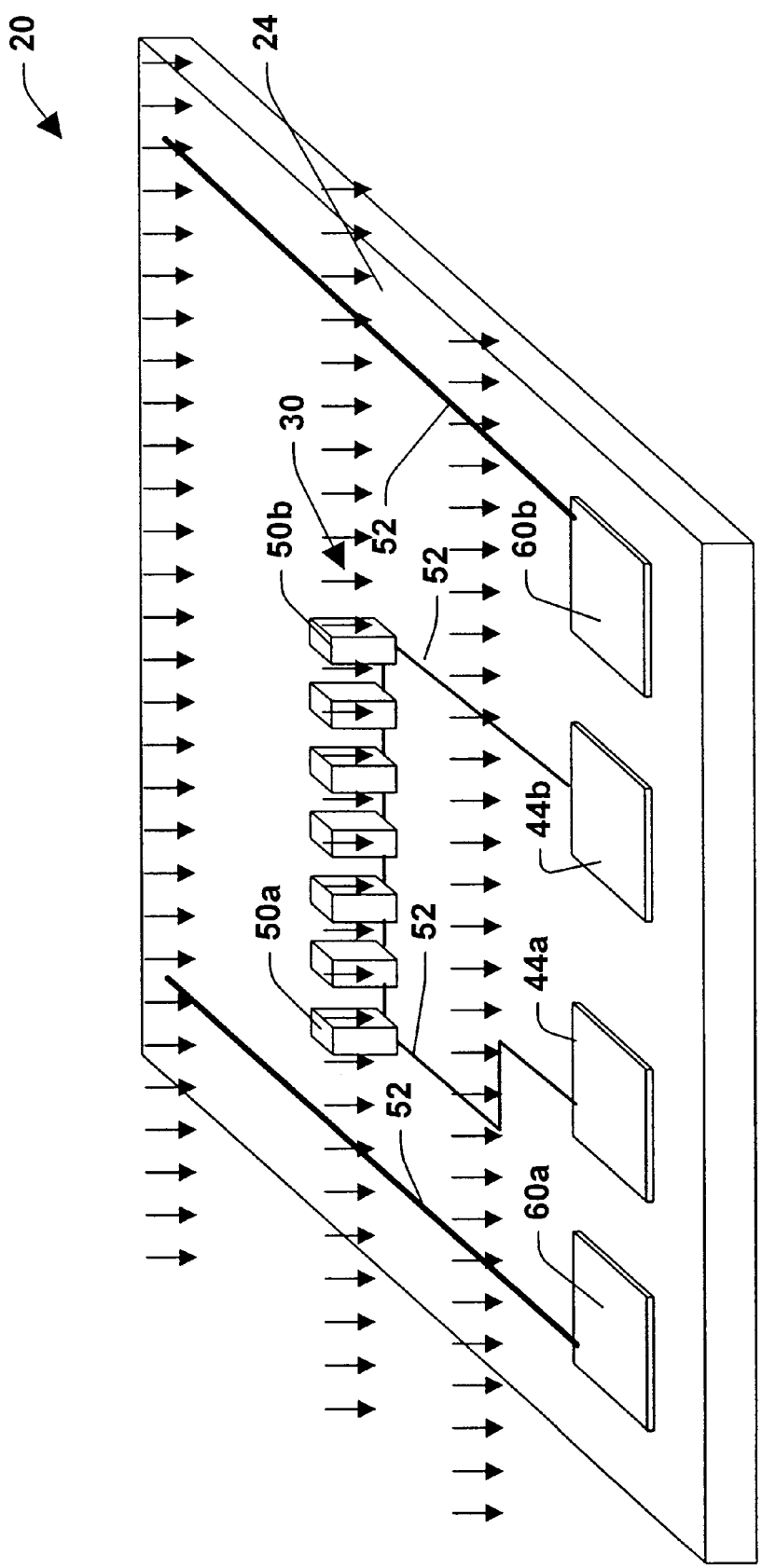
FIG. 9 is a perspective illustration of the substrate of FIG. 8 being masked, etched and patterned to form electrical contacts and electrical pathways in accordance with one embodiment of the present invention.

Turning now to FIG. 9, second masking and patterning steps are performed to form the electrical contacts 44a, 44b, 60a and 60b. A layer of resistive metal such as gold, platinum, nickel, aluminum, etc. is applied to the base 24 by a suitable process such as sputtering. The resistive metal layer is selectively etched by ion milling to form the electrical contacts 44a, 44b, 60a and 60b and conductive pathways 52.

Figure 10:
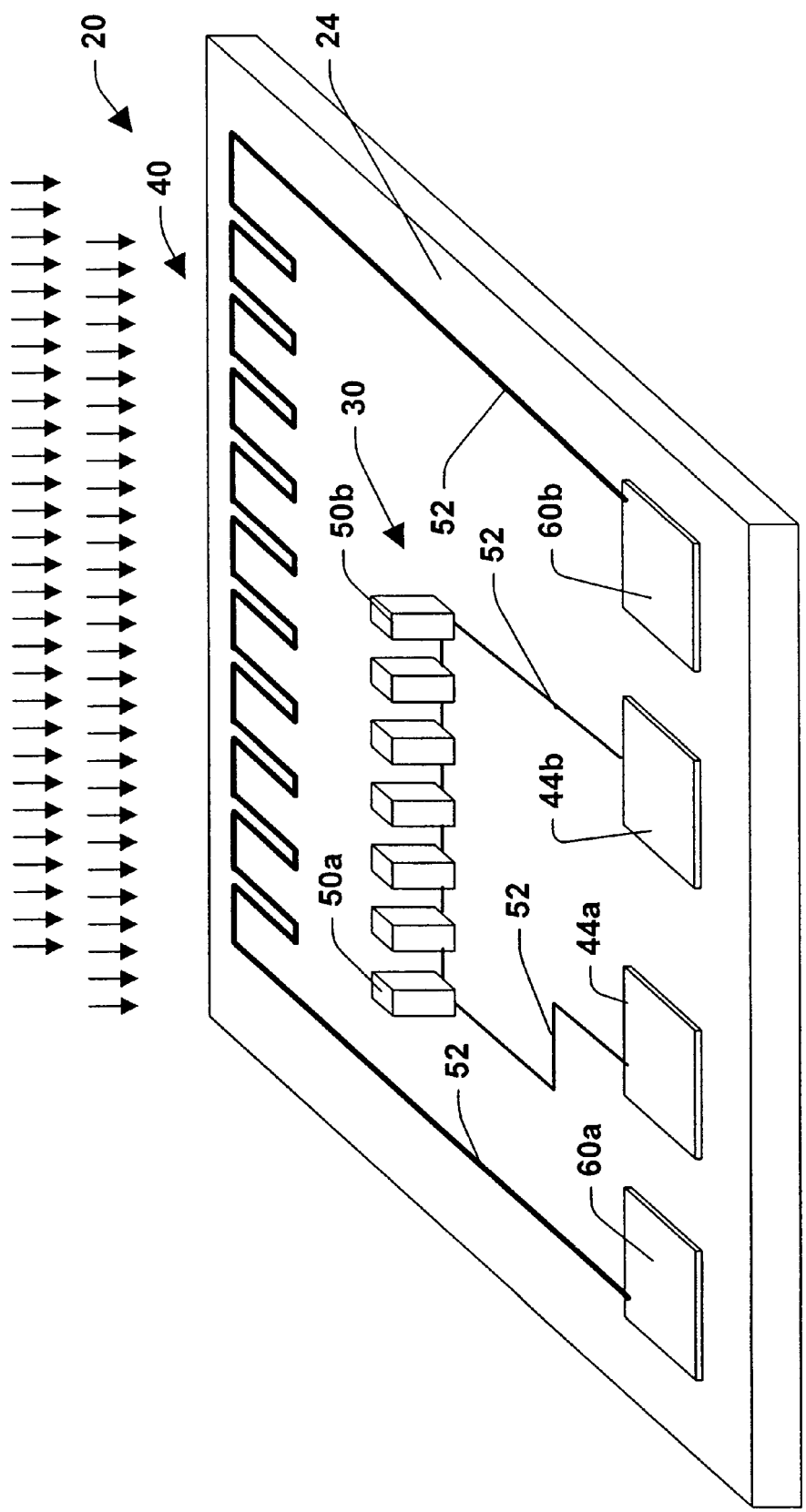
FIG. 10 is a perspective illustration of the substrate of FIG. 9 being masked, etched and patterned to form a temperature detector in accordance with one embodiment of the present invention.

Next in FIG. 10, third masking and patterning steps are performed to form the temperature detector 40. Preferably, platinum is employed in the formation of the temperature sensor 40, however, any material suitable for carrying out the present invention may be employed. It is to be appreciated that the steps of FIGS. 9–10 may be combined into a single step where the temperature detector 40 is fabricated at the same time as the electrical contacts 44a, 44b, 60a and 60b and conductive pathways 52.

FIG. 11 illustrates a subsequent step of seeding the array of finger-like elements with a seed layer 310 of metal, or dual combination of metals such as gold or palladium on top of chrome which is deposited on the array 30. Silicon is generally not a desired material to electroplate directly onto, and thus the seed layer is initially deposited over the array to facilitate plating (e.g., electroplating) of the array 30. Once the seed layer 310 coats the array of finger-like elements 30, the array 30 is prepared for plating in FIG. 12.

The plating 320 of the array 30 includes the use of either electroplating or electroless plating techniques. In the preferred embodiment, the array 30 is electroplated with Nickel.

The plating of the array 30 substantially completes the fabrication of the viscosity sensor shown as shown in FIG. 1.

Although the present invention has been described primarily in the context of a preferred embodiment, it is to be appreciated that the present invention may be carried out in other embodiments. For instance, FIG. 13 illustrates a front view of an alternative embodiment of a viscosity sensor 350 in accordance with the present invention. In this embodiment, both top and bottom sides of a base 360 include arrays of finger-like elements 362a and 362b, sets of electrical contacts 372a, 374a, 376a, 378a and 372b, 374b, 376b and 378b, and temperature detectors (not shown). As noted above, such an embodiment enhances the functional scope of the present invention by doubling the amount of sensitive components of the viscosity sensor.

Figure 14:
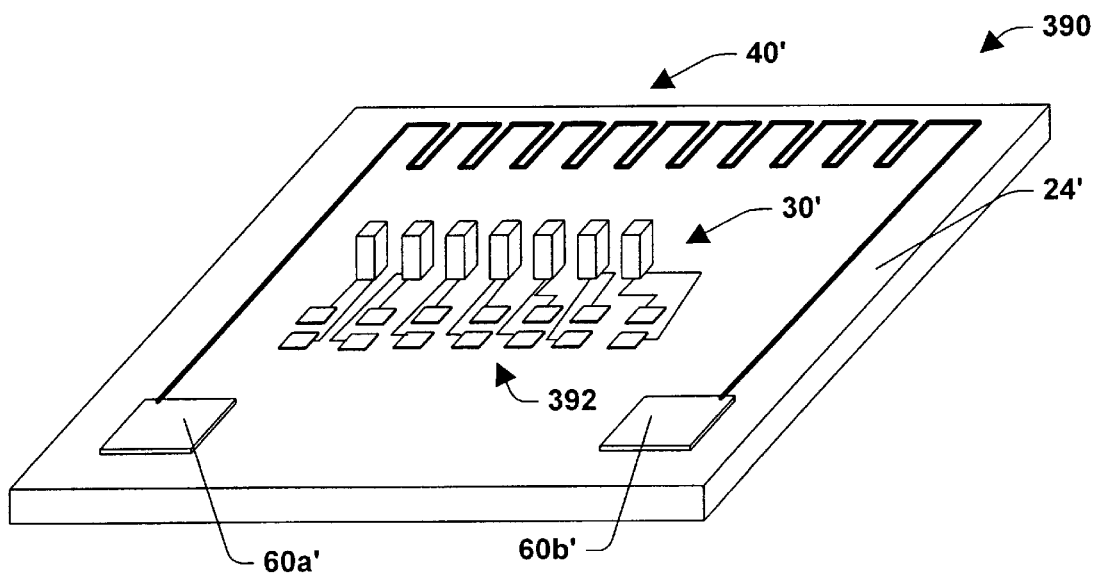
FIG. 14 is a perspective view of yet another viscosity sensor in accordance with an embodiment of the present invention.

FIG. 14 illustrates another embodiment of the present invention that is similar to the embodiment of FIG. 1. Accordingly, like components between the embodiments of FIGS. 1 and 14 include like reference numerals wherein the like components of FIG. 14 also including a prime ('). Repeated discussion relating to the like components is omitted for sake of brevity. In the viscosity sensor 390 of this embodiment, each finger-like element of the array 30' operates substantially autonomously from the other finger-like elements. Accordingly, a plurality of electrical contacts 392 are provided such that each finger-like element has its own set of input and output contacts. This feature provides for the viscosity sensor 390 to have enhanced redundancy of data collected with respect to that which is derived from the array of finger-like elements 30'. Thus, even if one finger-like element of the array 30' fails due to for example particle contamination sufficient amount of data may be gathered from the remaining properly functioning finger-like elements of the array 30'.

Figure 15:
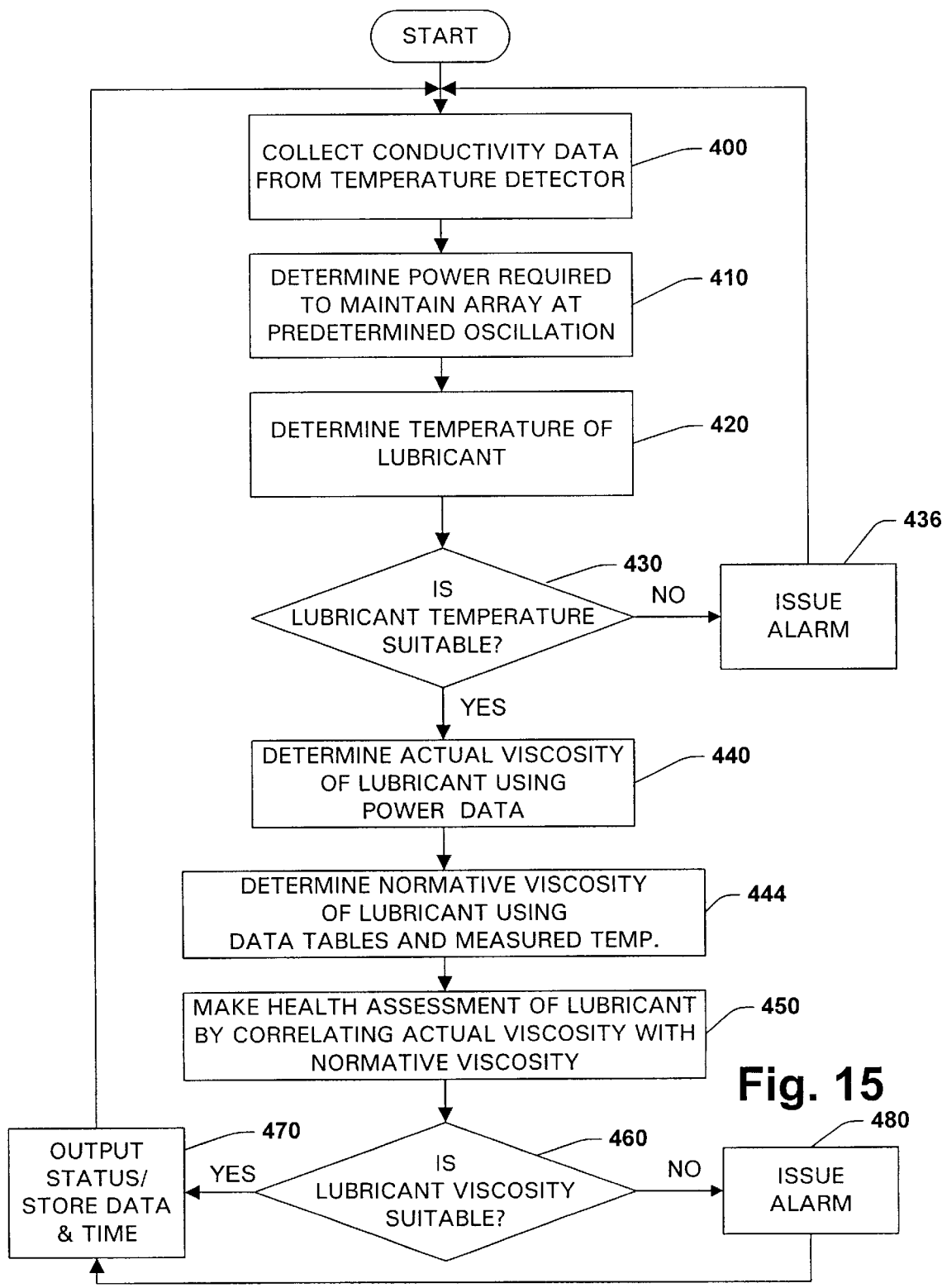
FIG. 15 is a flow diagram illustrating one methodology for carrying out the present invention.

FIG. 15 is a flow diagram illustrating one exemplary methodology for carrying out the present invention. In step 400, conductivity data is collected from the temperature detector 40. In step 410, the power required to oscillate the array 30 is determined. In step 420, the lubricant analyzer 90 determines the temperature of the lubricant based on the conductivity of the temperature detector 40. In step 430, the lubricant analyzer determines if the lubricant temperature is suitable. If no, the lubricant analyzer 90 issues a warning at step 435. If yes, in step 440 the lubricant analyzer 90 determines the actual viscosity of the lubricant using power data. In step 444, the lubricant analyzer 90 determines a normative viscosity level for the lubricant using data tables and measured temperatures. The normative viscosity level is a preferred/desired viscosity level corresponding to the type of lubricant, the specific application of the lubricant and measured temperature. In step 450, the lubricant analyzer 90 (employing its adaptive processor 198) makes a health assessment of the lubricant by correlating actual viscosity (step 440) with normative viscosity (step 444). In step 460, the lubricant analyzer 90 determines whether or not the viscosity level is suitable. If yes, the process proceeds to step 470 where the status of the lubricant is output, the lubricant data is stored and date stamped. If no, the process proceeds to step 480 where an alarm is issued. Thereafter, the process proceeds to step 470. The process then returns to step 400 to be repeated.

Although, the present invention has been described with respect to sensing and analysis of a lubricant, it is to be appreciated that the present invention provides for in situ monitoring of any suitable fluid where knowledge of the viscosity thereof is desired.

Figure 16:
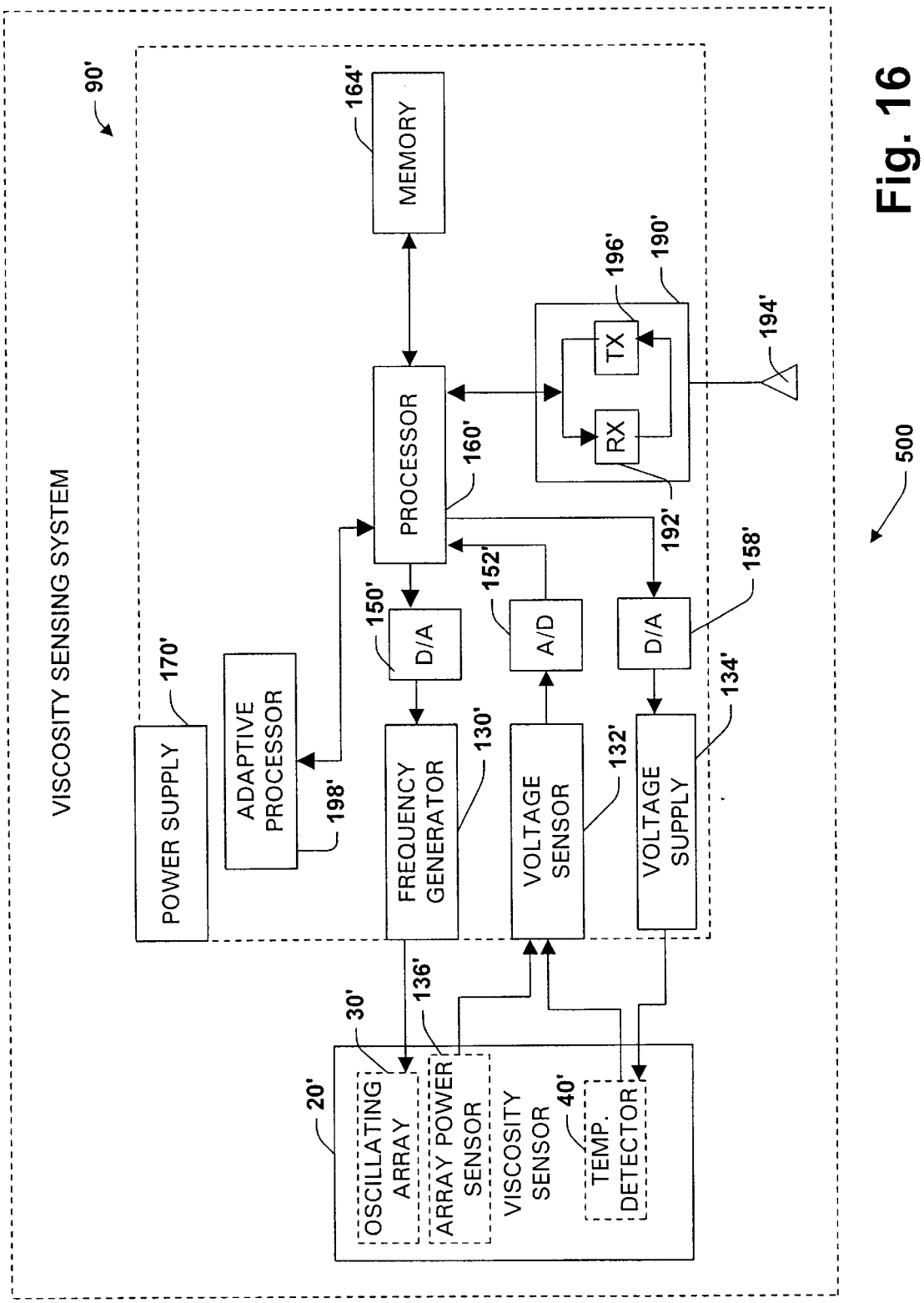
FIG. 16 is a schematic block diagram of an integrated viscosity sensing system in accordance with the present invention.

FIG. 16 is a schematic block diagram of an integrated viscosity sensing system 500 in accordance with the present invention. The components are essentially the same as that of the embodiment depicted in FIG. 3, accordingly like components in FIG. 16 include like reference numerals of FIG. 3 followed with an (') thereafter. However, the viscosity sensing system 500 does not include a display, display driver, operator input device or LAN interface because of the miniature nature of the viscosity sensing system 500. In the embodiment of FIG. 3, the analyzer 90 may be located remote from the viscosity sensor 20. In the integrated viscosity system 500, the analyzer 90' is integrated onto a semiconductor chip for example along with the viscosity sensor 20'. As a result, the integrated viscosity sensing system 500 provides for autonomous data collection and analyses directly at the location of the fluid being sensed. The memory 164' will provide for storing trending data, historical data and the like for employment during analysis of the fluid. The power supply 170' is chosen to be suitable for such in situ monitoring of the fluid (e.g., battery power, thermal power, fluid flow power).

The viscosity sensing system 500 may be embedded into a bearing for example and collect data relating to the viscosity of a fluid the bearing is exposed to. The viscosity sensing system 500 may perform all analyses necessary to determine the health state of the fluid and then transmit the results of the analyses via a wireless communications link to a remote device if desired.

Furthermore, although the present invention has been described with respect to a certain shape for the elements 30, it is to be appreciated that any suitable shape for carrying out the present invention may be employed. For example, the elements 30 may take the shape of a pyramid, donut, cylinder, semi-cylindrical, block, spherical, semi-spherical, cantilevered beam, membrane, diaphragm shaped, deforming structures, tilting structures, rotating disk, polygon cylinder, windmill shaped, fam shaped, etc. Moreover, it is to be appreciated that multiple devices of any of these shapes may be employed to carry out the present invention as well as various combinations (mixtures) of the different shaped elements may be employed.

Additionally, it will be appreciated that other analytical tools may be employed in carrying out the present invention. For example, rather than determining viscosity as a function of power draw as described above, amplitude and phase shift changes relating to signals input and output respectively from the array of elements 30 may be employed to determine viscosity of a fluid.

What has been described above are preferred embodiments of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A micro-viscosity sensor for sensing the viscosity of a fluid, comprising:
   at least one sensing element on a semiconductor base exposed to the fluid, the at least one sensing element adapted to be oscillated over a range of frequencies as driven by an electrical power applied thereto;
   wherein the viscosity of the fluid is determined as a function of the power required to maintain oscillation of the at least one sensing element at a predetermined frequency, the predetermined frequecy being different than a natural resonant frequency of the at least one sensing element.

2. The micro-viscosity sensor of claim 1 further including a temperature detector for detecting the temperature of the fluid.

3. The micro-viscosity sensor of claim 2; wherein the temperature of the fluid is correlated with the viscosity of the fluid to determine the health of the fluid.

4. The micro-viscosity sensor of claim 1, wherein the lubricant is one of: oil, grease hydraulic fluid and cutting oil/cutting coolant.

5. A micro-viscosity sensor for sensing the viscosity of a fluid, comprising:
   an array of finger-like elements vertically extending from the surface of a semiconductor base, the array of finger-like elements being oscillated at a pre-determined frequencies driven by an electrical power appleid thereto;
   wherein the power required to maintain oscillation of the array of finger-like elements at the pre-determined frequency corresponds to the viscosity of the fluid.

6. The micro-viscosity sensor of claim 5 further including a temperature detector for detecting the temperature of the fluid.

7. The micro-viscosity sensor of claim 6; wherein the temperature of the fluid is correlated with the viscosity of the fluid to determine the health of the fluid.

8. The micro-viscosity sensor of claim 5, the array of finger-like elements being plated with a conductive material.

9. The micro-viscosity sensor of claim 5, wherein the fluid is a lubricant.

10. The micro-viscosity sensor of claim 5, wherein the lubricant is one of: oil, grease hydraulic fluid and cutting oil/cutting coolant.

11. A lubricant analysis system, comprising:
    at least one micro-viscosity sensor, including:
       an array of finger-like elements extending perpendicular to the surface of a semiconductor base, the array of finger-like elements being oscillated at a predetermined frequency as driven by an electrical power applied thereto, wherein the power required to maintain oscillation of the array of finger-like elements at the pre-determined frequency corresponds to the viscosity of the fluid, the pre-determined frequency being different than a natural resonant frequency of the finger-like elements;
    a lubrication analyzer, including:
       a processor operatively coupled to the at least one micro-viscosity sensor, the processor adapted to process data output from the at least one micro-viscosity sensor to determine the viscosity of the fluid.

12. The system of claim 11, the lubrication analyzer further including a frequency generator.

13. The system of claim 11, the at least one micro-viscosity sensor further including a temperature detector, wherein the electrical conductivity of the temperature detector varies in correspondence with the temperature of the lubricant.

14. The system of claim 13, the lubrication analyzer further including a voltage sensor operatively coupled to the temperature detector, wherein the processor determines the temperature of the lubricant based on the voltage output of the voltage sensor.

15. The system of claim 11, the lubrication analyzer including a memory operatively coupled to the processor, the memory storing at least one lookup table comprising historical data relating to lubricant viscosity.

16. The system of claim 11, further including a host computer operatively coupled to the lubrication analyzer.

17. The system of claim 16, the lubrication analyzer including a neural network.

18. The system of claim 16, the lubrication analyzer including an expert system.

19. The system of claim 16, the lubrication analyzer including an adaptive processor to facilitate health assessment of the lubricant.

20. A method for fabricating a micro-viscosity sensor, comprising the steps of:
    etching a semiconductor substrate to form an array of finger-like elements which extend perpendicularly from a base of the substrate, the array of finger-like elements adapted to oscillate over a range of frequencies as driven by an electrical power apllied thereto, wherein the power required to maintain oscillation of the array of finger-like elements at a particular frequency corresponds to the viscosity of a fluid being sensed, the particular frequency being different than a natural resonant frequency of the array of finger-ike elements.

21. The method of claim 20, further including the step of forming a temperature detector on the base.

22. The method of claim 20, further including the step of forming electrical contacts.

23. The method of claim 20, further including the step of forming electrical connection pathways.

24. The method of claim 20, further including the step of plating the array of finger-like elements.

25. The method of claim 20, further including the step of forming a second array of finger-like elements on the other side of the base, the second array of finger-like elements adapted to oscillate over a range of frequencies, wherein the power required to maintain oscillation of the array of second array of finger-like elements at a particular frequency corresponds to the viscosity of the fluid being sensed.

26. A micro-viscosity sensor for measuring the viscosity of a lubricant, comprising:

at least one finger-like element extending from the surface of a semiconductor base, the at least one finger-like element operative to be oscillated over a range of frequencies as driven by an electrical power applied thereto;

a temperature detector, wherein the conductivity of the temperature detector varies in correspondence with the temperature of the lubricant;

a first set of electrical contacts for providing electrical connection to the at least one finger-like element; and a second set of electrical contacts for providing electrical connection to the temperature detector;

wherein the power required to maintain oscillation of the at least one finger-like element at a particular frequency corresponds to the viscosity of the fluid being sensed, the particular freqency being different than a natural resonant frequency of the at least one finger-like element.

27. The micro-viscosity sensor of claim 26, wherein the temperature sensor comprises at least one of gold, palladium, platinum, nickel and aluminum.

28. The micro-viscosity sensor of claim 26 operatively coupled to a lubrication analyzer, including a processor operatively coupled to the at least one finger-like element and the temperature detector, the processor adapted to process data output from the micro-viscosity sensor to determine the viscosity of the lubricant.

29. The micro-viscosity sensor of claim 26 wherein the lubricant is employed to lubricate at least one bearing of a dynamoelectric machine.

30. The micro-viscosity sensor of claim 26 used in a forced lube system.

31. The micro-viscosity sensor of claim 26 used in a gear box.

32. The micro-viscosity sensor of claim 26 used in connection with hydrodynamic bearings.

33. The micro-viscosity sensor of claim 26 used in connection with a bearing system.

34. The micro-viscosity sensor of claim 26 providing for in situ sensing of the fluid.

35. A method for sensing the viscosity of a fluid, comprising the steps of:

oscillating at least one element extending from the surface of a semiconductor base, the at least one element operative to be oscillated over a range of frequencies as driven by an electrical power applied thereto;

using a temperature detector to measure the temperature of the fluid, wherein the conductivity of the temperature detector varies in correspondence with the temperature of the lubricant; and determining the power required to maintain oscillation of the at least one element at a particular frequency, the particular frequency being different than a natural resonant frequency of the at least one element:

wherein the power required is a function of the viscosity of the fluid.

36. A viscosity sensing system, comprising:

at least one micro-viscosity sensor, including:

an array of finger-like elements extending from the surface of a semiconductor base, the array of elements finger-like being oscillated at a predetermined frequency, wherein the power required to maintain oscillation of the array of finger-like elements at the pre-determined frequency corresponds to the viscosity of the fluid;

a lubrication analyzer, including:

a processor operatively coupled to the at least one micro-viscosity sensor, the processor adapted to process data output from the at least one micro-viscosity sensor to determine the viscosity of the fluid wherein the integrated viscosity sensing system provides for in situ monitoring of the fluid.

* * * * *